United States Patent [19]

Kinson et al.

[11] 4,058,570

[45] Nov. 15, 1977

[54] BROMINATED BIPHENOL PROCESS

[75] Inventors: Philip L. Kinson, Rexford; Charles M. Orlando, Schenectady, both of N.Y.

[73] Assignee: General Electric Company, Schenectady, N.Y.

[21] Appl. No.: 684,175

[22] Filed: May 7, 1976

Related U.S. Application Data

[63] Continuation-in-part of Ser. No. 533,948, Dec. 18, 1974, abandoned.

[51] Int. Cl.$^2$ .................... C07C 37/00; C07C 41/00; C07C 49/62
[52] U.S. Cl. .............................. 260/620; 260/613 R
[58] Field of Search ............... 260/620, 612 R, 613 R

[56] References Cited

U.S. PATENT DOCUMENTS

| | | | |
|---|---|---|---|
| 3,546,302 | 12/1970 | Asadonan et al. | 260/620 |
| 3,720,721 | 3/1973 | Becker et al. | 260/620 |
| 3,748,303 | 7/1973 | Becker et al. | 260/620 |
| 3,894,094 | 7/1975 | Rutledge | 260/620 |
| 3,929,908 | 12/1975 | Orlando et al. | 260/620 |
| 3,956,403 | 5/1976 | Orlando et al. | 269/620 |

*Primary Examiner*—Norman Morgenstern
*Attorney, Agent, or Firm*—F. Wesley Turner; Joseph T. Cohen; Jerome C. Squillaro

[57] ABSTRACT

Brominated biphenols are produced by a bromination process which comprises reacting bromine with a 3,3', 5,5'-tetrasubstituted diphenoquinone at a temperature below about +20° C. in the presence of an inert diluent, evolving hydrogen bromide gas at a temperature of about +20° C. or lower, heating the resulting reaction mixture at elevated temperatures to complete the bromination reaction and recovering the desired 2,2',6,6'-tetrabromo-3,3',5,5'-tetrasubstituted-4,4'-biphenol. The biphenol products of the process can be used as antioxidants, as monomeric starting materials for polymeric halogenated organic compounds which are fire retardant as well as monomeric flame retardant additives for polymeric compositions useful in molding, coating and insulating various articles of manufacture.

9 Claims, No Drawings

BROMINATED BIPHENOL PROCESS

This is a continuation-in-part of application Ser. No. 533,948, filed Dec. 18, 1974 now abandoned.

This invention relates to an improved process for the preparation of 2,2', 6,6'-tetrabromo-3,3', 5,5'-tetrasubstituted-4,4'-biphenols which comprises the bromination of 3,3', 5,5'-tetrasubstituted diphenoquinone by initiating the reaction of the latter with bromine at a temperature at least below about +20° C. in the presence of an inert diluent, evolving hydrogen bromide gas at a temperature of about +20° C. or lower and recovering the desired 2,2', 6,6'-tetrabromo-3,3', 5,5'-tetrasubstituted-4,4'-biphenol.

Various observations have been made by the prior art regarding reactions between bromine and 3,3', 5,5'-tetrasubstituted diphenoquinone carried out in both the presence and the absence of inert liquid solvents, such as those described in Orlando et al., U.S. patent application Ser. No. 169,517, filed Aug. 5, 1971, now U.S. Pat. No. 3,929,908 assigned to the same assignee as the assignee of this invention.

In general, following the teachings of the prior art, it was found during bromination of 3,3', 5,5'-tetrasubstituted diphenoquinones in the absence of any inert diluent at about ambient room temperatures (25° C.) while cooling the reaction media and controlling the rate of addition of the diphenoquinone so as to avoid an uncontrolled exothermic reaction, that when the bromination process was carried out under 400–500 gram end product scale — in the presence of large excesses of bromine in order to retain a liquid phase reaction medium at all times — that the yield of the desired end product, 2,2', 6,6'-tetrabromo-3,3', 5,5'-tetrasubstituted-4,4'-biphenol (TTB) was no greater than about 40% of theory based on conversion of 100% of the amount of diphenoquinone reactant charge. Unexpectedly, it has been found that the yield of TTB can be substantially improved from prior art yields of about 40% to yields of about 70% or even greater wherein bromine is added to a mixture of 3,3', 5,5'-tetrasubstituted diphenoquinone (TSDQ) in the presence of a diluent wherein the addition of bromine is carried out at temperatures below about +20° C.

Further the prior art has neither taught or recognized that (a) when the bromination reaction is initiated at reaction temperatures lower than about +15° C. that substantial amounts of hydrogen bromide gas are not evolved from the reaction mixture until the reaction temperature reaches approximately +15° C. or higher, or (b) that even though the reaction is initiated at temperatures of about +15° C. or lower that unless the bromine to diphenoquinone mole ratios are limited, i.e. lower than about 6.5:1, respectively, that as the reaction temperature increases essentially uncontrolled HBr evolution occurs which causes explosive reaction pressure peaks. Further, unexpectedly, it has also been found that (a) when the bromination of TSDQ is initiated at temperatures lower than about +15° C. in the presence of limited amounts of bromine to diphenoquinone mole ratios, i.e. lower than about 6.5:1, that gaseous hydrogen bromide evolves from the reaction mixture at substantially controlled evolution rates without encountering run-away reaction pressure process conditions, and (b) that the overall reaction time period required for substantial conversion of the TSDQ to TTB, e.g. 70% or greater yields, is substantially reduced.

Essentially, this invention comprises the bromination of 3,3', 5,5'-tetrasubstituted diphenoquinone at a temperature lower than about +20° C. in the presence of a diluent evolving hydrogen bromide gas at a temperature of up to about +20° C. and recovering the desired 2,2', 6,6'-tetrabromo-3,3', 5,5'-tetrasubstituted-4,4'-phenol.

Another embodiment of this invention comprises the bromination of a 3,3', 5,5'-tetrasubstituted diphenoquinone by reacting the latter with bromine at a temperature lower than about +20° C. in the presence of a diluent wherein the bromine to diphenoquinone mole ratio is lower than about 6.5 to 1, respectively, initiating and maintaining the evolution of gaseous hydrogen bromide at a substantially controlled rate at a temperature up to about +20° C., contacting the resulting reaction mixture with additional bromine, heating the reaction mixture at elevated temperatures to complete the bromination reaction, and recovering 2,2', 6,6'-tetrabromo-3,3', 5,5'-tetrasubstituted-4,4'-biphenol.

In this process, any 3,3', 5,5'-tetrasubstituted diphenoquinone (TSDQ) or mixtures thereof can be reacted with bromine. Representative of TSDQ compounds are those described by the general formula:

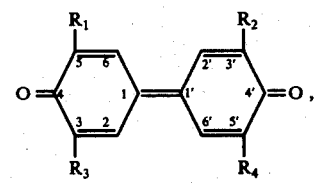

wherein independently each $R_1$, $R_2$, $R_3$ and $R_4$ substituent is a primary lower alkyl, primary lower alkoxy, phenyl, or 4-bromophenyl. Representative substituents include methyl, methoxy, ethyl, ethoxy, propyl, propoxy, butyl, butoxy, phenyl, phenoxy, hexyl, hexoxy, cyclohexyl, cyclohexoxy, heptyl, heptoxy, octyl, octoxy, etc. Although aryl substituents other than phenyl can be substituents on the diphenoquinone, such diphenoquinones are not readily available and therefore we prefer the aryl substituents to be phenyl. Generally, the diphenoquinones preferably employed contain from 16 to about 40, more preferably from 16 to 28 carbon atoms. Especially preferred diphenoquinones are 3,3', 5,5'-tetraalkyldiphenoquinones wherein each substituent is an alkyl group containing from 1 to 4 carbon atoms. More especially preferred is 3,3', 5,5'-tetramethyl diphenoquinone since this tetramethyl diphenoquinone is presently the most readily available tetraalkylsubstituted diphenoquinone.

Any 2,2', 6,6'-tetrabromo-3,3', 5,5'-tetrasubstituted-4,4'-biphenol (TTB) or mixtures thereof can be obtained by the reaction of bromine with TSDQ. Representative of TTB compounds are those described by the general formula:

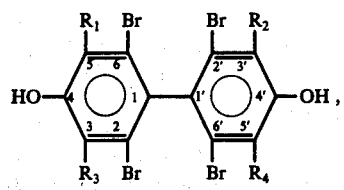

wherein $R_1$, $R_2$, $R_3$ and $R_4$ are defined as above with respect to the TSDQ general formula. Although other brominated biphenols are formed — wherein the degree of bromination is less or more than four bromide atoms per molecule of diphenoquinone as reaction products or reaction intermediates — the process of this invention provides yields of up to at least about 70% or even higher of TTB based based on 100% conversion of TSDQ.

Essential to the practice of this invention is the reaction of bromine with diphenoquinone at temperatures substantially below ambient room temperature, i.e. temperatures below about +20° C. at least low enough to substantially limit the evolution of hydrogen bromine gas during the initial bromine TSDQ contact. Preferred are reaction temperatures lower than about +15° C., more preferred lower than about +10° C., even more preferred lower than about 0° C., such as −20° C., or even lower subject to the proviso that at least a portion of the liquid bromine-inert diluent phase, preferably substantially all of the liquid phase, does not solidify.

Any mole proportion of bromine to diphenoquinone can be employed subject to the proviso that the bromine ($Br_2$) be available in stoichiometric quantities theoretically required for 100% conversion of the TSDQ to TTB. Accordingly, the total $Br_2$:TSDQ mole proportion employed is at least equal to or greater than about 2.0:1, however can be as large as 3.0:1, 4.5:1, 6.5:1, 10.1,15:1, etc., or even higher.

In general, after initial contact of the diphenoquinone with at least a portion of the total bromine reactant at reduced temperatures, the temperature of the reaction mixture gradually increases due to the exothermic nature of the reaction and gaseous HBr evolution begins. Following HBr evolution, the mixture may be heated in order to rapidly complete the bromination reaction and yield the desired TTB end product. In general, completion of the reaction can be carried out by heating the reaction mixture within the range at which gaseous HBr evolution begins, e.g. about +15° C., to bromine-diluent reflux temperatures, e.g. +60° C., or even higher.

Where a reduction in the maximum rate of evolution of gaseous hydrogen bromide and the ability to operate under substantially controlled gaseous hydrogen bromide evolution rates is desired, optionally and preferably, the initial quantity of bromine available to react wtih TSDQ is limited to a $Br_2$:TSDQ mole ratio equal to or less than about 6.5:1, preferably, less than 4.5:1, and more preferably less than 2.5:1. The reason that limited amounts of bromine are provided during the initial contact of the diphenoquinone (first step) at temperatures at least lower than about +20° C. is based on the unexpected finding that a first step reaction time period and the maximum rate of evolution of gaseous hydrogen bromide — including any induction period prior to the evolution of gaseous hydrogen bromide — decreases as the mole proportion of $Br_2$:TSDQ employed in the first step is decreased. A first step reaction time period is defined herein as the elapsed time period encompassing the period of time measured from the initial contact of TSDQ with bromine until the hydrogen bromine gas is evolved at temperatures up to about +20° C. Following the evolution of at least a substantial portion of hydrogen bromide gas which evolves during the first step from the reaction media at a temperature of at least about +15° C., the second step of the process is initiated wherein additional bromine is charged to the reaction media in quantities at least sufficient to provide a total reaction $Br_2$:TSDQ mole ratio at least greater than about 6.5:1, preferably 8.5:1 and even more preferably of 10:1, 15:1 or even higher. The complete conversion of the reactants to TTB can readily be carried out by heating the reaction mixture as described hereinbefore. In general, in the first step wherein the TSDQ liquid diluent mixture is contacted with bromine, the bromination reaction takes place in a heterogeneous viscous slurry. Preferably, the reaction medium is agitated by mechanical or some other suitable means in order to maintain at least a substantially uniform dispersion of TSDQ and reaction intermediates within any heterogeneous and/or homogeneous phase(s) of the reaction medium. Although the process can be carried out in the presence of a liquid diluent in both the first and second steps (initial and later bromine contact periods), it is possible to carry out the second step in the absence of any diluent and still obtain the high yields associated with the practice of this invention. This diluent first step - no diluent second step method can be employed by using a diluent having a boiling point lower than bromine in the first step, removing the diluent after completing the first step while maintaining the intermediate reaction products in solution in bromine, adding addition bromine and thereafter heating the resulting solution to complete the reaction.

Any (essentially nonreactive) liquid diluent can be employed providing that bromine and the diluent form at least a partially miscible liquid phase. Any amount of diluent can be employed providing that at least sufficient volumes are available to provide a suspension of TSDQ in the diluent. Preferably, the amount of diluent employed is such that the volume of bromine is approximately equal to the volume of inert liquid of the reaction media. Accordingly, the volume proportion of bromine ($Br_2$) to diluent (D) is at least within the range of from about 2.25:1 to about 1:2.25 preferably from about 1.5:1 to about 1:1.5, and even more preferably from about 1.25:1 to about 1:1.25. The preference for the employment of the relative volume ranges of bromine to diluents, set out hereinbefore, is associated with the finding that such proportions aid in the acquisition of the TTB yields obtained by the practice of this invention. Preferred diluents employed in the process are essentialy nonreactive halogenated hydrocarbons such as relatively low boiling halogenated aliphatic hydrocarbons, e.g. carbon tetrachloride, chloroform, methylene chloride, tribromomethane, bromotrichloromethane, trichloroethane, etc., among others.

Following the completion of the reaction, tetrabrominated biphenol reaction product can be recovered from reaction medium by any suitable means of separating bromine and diluent from the resulting reaction product. For example, where a diluent such as carbon tetrachloride is used, which has a higher boiling point than bromine, any unreacted excess bromine can be removed from the reaction media by codistilling $Br_2$ and $CCl_4$ at reflux temperatures while concurrently replacing the distillate volume of $Br_2$ and $CCl_4$ with approximately an equivalent volume of $CCl_4$. A presently preferred method of separating TTB employs steam distillation techniques since this technique removes bromine from the reaction medium at elevated temperatures more efficiently and more rapidly than codistillation techniques. In addition, TTB products recovered when steam distillation techniques are employed are lighter in color, contain fewer undesirable by-products (e.g. penta-, hexa-, etc., brominated biphenols including any by-products derived therefrom).

The 3,3', 5,5'-tetrasubstituted diphenoquinone starting materials can be prepared by any means known to those skilled in the art including the methods described by Finkbeiner et al. in U.S. patent application Ser. No. 417,145, filed Nov. 19, 1973, and by Hay in U.S. Pat. No. 3,306,875, issued Feb. 28, 1967, both assigned to the same assignee as the assignee of this invention. These methods essentially involve the oxidative coupling of a 2,6-disubstituted phenol using a basic cupric salt-amine complex. In the practice of this invention, we prefer to use those diphenoquinones where all four substituents are identical or the two substituents on one of the rings are different but are the same as the two substituents on the other ring.

In order that those skilled in the art may better understand this invention, the following general procedure and examples are given which illustrate the best mode of practicing this invention, however, neither the general procedures nor the examples are intended to limit the invention in any manner whatsoever. In all of the examples, unless otherwise stated, the following general procedures were employed and all parts are by weight. For purposes of brevity, only deviations from the general procedures will be set out in the examples.

GENERAL PROCEDURE
EXAMPLES I AND II a. Single Step

A suspension of a 3,3', 5,5'-tetrasubstituted diphenoquinone, e.g. tetramethyl diphenoquinone dispersed in an inert liquid diluent, e.g. carbon tetrachloride, is charged into a reactor, e.g. a jacketed 5-gallon glass-lined Pfaudler reactor equipped with a stirrer, distilling tower and condenser. The diphenoquinone-diluent slurry is precooled to temperatures below +20° C., e.g. −15° C. Liquid bromine is added to the cooled TSDQ suspension and the reaction media temperature increases, due to the exothermic nature of the reaction, to a temperature of about 0° C., e.g., +1° C. The reaction mixture temperature is allowed to gradually rise to elevated temperatures, e.g. about 20° C. during an extended period of time, e.g. about 2¾ hours. As the reaction mixture reaches about +15° C. a controlled but sustained hydrogen bromide gas evolution occurs. When the hydrogen bromide gas evolution begins to subside, the reaction mixture is heated for about an hour. The bromine and diluent are codistilled at reflux temperatures, e.g. about +60° C. to +75° C. After codistillation of approximately 50% by volume of the bromine and diluent, additional diluent is added. Removal of bromine by codistillation is completed in about 3⅛ hours. The resulting crude TTB is isolated as a suspension in the diluent. The suspension is cooled to room temperature and filtered. Crude TTB product is reslurried with a suitable solvent, e.g. hot acetone, cooled and filtered. The purified product is dried overnight under vacuum at elevated temperatures, e.g. about +100° C. The purified TTB product, e.g. 2,2', 6,6'-tetrabromo-3,3', -5,5'-tetrasubstituted biphenol is characterized by its melting point, mass spectrum and nuclear magnetic resonance spectrum.

GENERAL PROCEDURE
EXAMPLES III AND IV b. Multiple Step

A 3,3', 5,5'-tetrasubstituted diphenoquinone, e.g. 3,3', 5,5'-tetramethyl diphenoquinone, and an inert diluent, e.g. carbon tetrachloride are charged to a round bottom flask, e.g. a 1,000 ml. flask fitted with a paddle stirrer, thermometer, additional funnel and a reflux condenser. The TSDQ and diluent are cooled to a temperature below ambient room temperature, e.g. temperatures within the range of from about −5° to about −15° C. Liquid bromide is added to the TSDQ diluent mixture during which time the exothermic nature of the reaction increases the reaction media temperature, e.g. to temperatures within the range of from about −9° to about +2° C., during which time no HBr gas is evolved from the reaction mixture. As the reaction mixture temperature increases, e.g. to temperatures of about +15° C., the viscosity of the reaction media increases. Prior to the evolution of HBr from the reaction mixture, the reaction mixture changes color, e.g. from green to red, and initial hydrogen bromide gas evolution from the reaction mixture occurs. After the evolution of hydrogen bromide gas from the reaction mixture, additional liquid bromine is added and the reaction temperature is gradually increased, e.g. up to bromine/diluent reflux temperatures of about 58° C. for a period of one hour, to complete the bromination reaction and yield the desired TTB reaction product, e.g. 2,2', 6,6'-tetrabromo-3,3', 5,5'-tetramethyl-4,4'-biphenol. The resulting TTB reaction product is separated from the reaction mixture by codistillation of the diluent in combination with excess bromine while concurrently replacing the distillate volume with equal volume of additional diluent. The resulting tetrabrominated biphenol is futher separated and purified by conventional procedures, e.g. filtration and trituration of the resulting filter cake with a suitable solvent, e.g. acetone, to yield the desired tetrabrominated biphenol product. The TTB is e.g. 2,2', 6,6'-tetrabromo-3,3', 5,5'-tetramethyl-4,4'-biphenol; characterized by its melting point, e.g. 246°–247° C. and recovered in substantial yield, e.g. 75% yield based on 100% conversion of TSDQ.

EXAMPLE I 2800 grams (11.6 moles) of 3,3', 5,5'-tetramethyl diphenoquinone and 8 liters of carbon tetrachloride were charged to the reactor. 8 liters (24.0 kilograms, 150 moles) of liquid bromine was added to the precooled mixture. After completion of the reaction, which was carried out in accordance with the General Procedure, a total of 4,676.4 grams (71.9% yield) of a white crystalline 2,2',6,6'-tetrabromo-3,3', 5,5'-tetramethyl-4,4'-biphenol was obtained. The product had a melting point of 246°–247° C.

EXAMPLE II

The results of a series of runs which were carried out in accordance with the General Procedure set out hereinbefore are tabulated and set out in Table I, Run Nos. 1 and 2.

TABLE I

| Run Numbers | 1 | 2 |
|---|---|---|
| Reaction Parameters | | |
| Mole Ratio $Br_2$:TMDQ | 11.4:1 | 11.4:1 |

TABLE I-continued

| Run Numbers | 1 | 2 |
|---|---|---|
| Br₂ Addition: | | |
| ml. | 250 | 250 |
| Time (Min.) | 12.8 | 36.0 |
| Temp. (° C.) | −14 to +1 | −14 to −9 |
| Heating Rate: | | |
| 0° C. to HBr Evolution (Min.) | 58 | 124 |
| Reaction Color Just Prior to HBr Evolution | Red | Red |
| HBr Evolution: | | |
| Time (Min.) | 73 | 174 |
| Temp. (° C.) | 24.5 to 21.1 | 21 to 16.3 |
| Reaction Time Sequence (Min.) | | |
| Br₂ Addition | 12.8 | 36.0 |
| After Br₂ Addition to Initial HBr Evolution | 61.4 | 139 |
| HBr Evolution | 40.3 | 72 |
| TOTAL | 174.5 | 307 |
| Overall Yield After Reaction and Isolation (%) | 74 | 75 |

As illustrated by the above data, yields of TTB of 71–75% can be obtained wherein the bromination reaction is carried out in the presence of large excesses of bromine and a diluent wherein bromine is added to TSDQ at temperatures below ambient room temperature.

EXAMPLE III

The results of a series of runs which were carried out in accordance with the General Procedure — Multiple Step are tabulated and set out hereafter in Table II, Run Nos. 3–5. Various reaction parameters were evaluated including first step variations in the mole proportions Br₂:TMDQ, bromine addition temperature range; bromine addition time period, the time period in which the temperature rose from approximately 0° C. to the temperature at which initial hydrogen bromide gas evolution occurred, and the color of the reaction mixture just prior to hydrogen bromide evolution.

TABLE II

Effect of Bromine Addition method on TTB Reaction

| Run Numbers | 3 | 4 | 5 |
|---|---|---|---|
| First Step Reaction Parameters | | | |
| Mole Ratio Br₂:TMDQ | 2.2:1 | 4.5:1 | 6.7:1 |
| Br₂ Addition: | | | |
| ml. | 50 | 100 | 150 |
| Time (Min.) | 5.9 | 6 | 24.6 |
| Temp. (° C.) | −15 to −2 | −14 to 0 | −14 to 0 |
| Percent (%) of Total Br₂ Charged | 20 | 40 | 60 |
| Heating Rate: | | | |
| 0° C. to HBr Evolution (Min.) | 5.5 | 27 | 31 |
| Reaction Color Just Prior to HBr Evolution | Green | Green | Red |
| HBr Evolution: | | | |
| Time (Min.) | 21.5 | 43 | 60.3 |
| Temp. (° C.) | 33.5 to 51 | 22.5 to 33 | 29 to 35 |
| Max. Rate (ml/min) | 283 | 280 | 2000 |
| Reaction Time Sequence | | | |
| (a) First Step | | | |
| Br₂ Addition | 5.9 | 6.0 | 24.6 |
| After Br₂ Addition to Initial HBr Evolution | 15.3 | 38 | 35.9 |
| HBr Evolution | 14.1 | 8 | 25.5 |
| (b) Second Step | | | |
| Br₂ Addition | 15.1 | 14 | 2 |
| TOTAL | 110.4 | 126 | 148 |
| Overall Yield After Reaction and Isolation (%) | — | 76 | 71 |

As illustrated by the above data, the HBr evolution rate and reaction time period vary in accordance with the initial first step Br₂:TMDQ reactant proportions.

EXAMPLE IV

A large scale of synthesis of 2,2′, 6,6′-tetrabromo-3,3′, 5,5′-tetramethyl-4,4′-dihydroxybiphenyl (also known as 2,2′, 6,6′-tetrabromo-3,3′, 5,5′-tetramethyl-4,4′-biphenol) was run on a semicommercial scale to evaluate the suitability of the process to semicommercial production of TTB. The reaction was carried out accordingly: a suspension of 3200 grams (13.3 moles) of 3,3′, 5,5′-tetramethyl diphenoquinone in 8 liters of carbon tetrachloride in a jacketed 5 gallon glass-lined Pfaudler reaction equipped with stirring, distilling tower and condenser was precooled to −10° C. (internal reactor temperature) using a dry ice/glycol/water coolant mixture. The internal reactor temperature was monitored with a conventional thermocouple-recorder system. A total of 3200 ml. (9600 grams, 60 moles) of bromine was then added to the cooled reaction mixture over a 20 minute period and the internal temperature rose to −8° C. A further increase in this temperature to +3° C. was observed during the next 20 minutes of stirring and the temperature then decreased to +1° C. after an additional 5 minutes. The cooling system was shut off to the jacket and water was slowly added to the jacket to gradually increase the internal temperature. During the next 87 minutes, the temperature rose to +27° C. whereupon a gradual evolution of hydrogen bromide occurred accompanied by a drop in internal temperature to +22° C. At this point 4800 ml. (14,400 grams, 90 moles) of bromine was added rapidly over a 15 minute period and steam heat was applied to the jacket to heat the reaction mixture. Within 46 minutes the reaction mixture was at reflux and held there for 1 hour. After this heating cycle the bromine-carbon tetrachloride mixture was distilled from the reactor. A total of 7 liters of distillate was taken and beginning with the next liter of distillate, each liter removed was replaced by addition of one liter of carbon tetrachloride to the reactor. After a total of 28 liters of distillate was replaced with 28 liters of carbon tetrachloride, the distillate contained very little bromine and the contents of the reactor was drained, cooled and filtered to give a tan solid. The entire wet cake was recharged to the reactor and 8 liters of acetone added and the mixture refluxed for one hour. The reaction mixture was cooled, drained, filtered and dried to give 5405 grams (72%) yield of 2,2', 6,6'-tetrabromo-3,3', 5,5'-tetramethyl-4,4'-biphenol.

The brominated biphenols of this invention can be used as antioxidants for petroleum products, such as gasoline and as stabilizers against polymerization of monomeric materials to maintain them in the essentially unpolymerized state until such time as they are ready for polymerization, for instance, with an organic peroxide. Further, as disclosed in the Orlando et al. copending U.S. patent applications Ser. Nos. 450,334, 450,364 and 169,517, filed Mar. 12, 1974, Mar. 12, 1974 and Aug. 5, 1971, respectively, assigned to the same assignee as the assignee of this invention, brominated biphenols can be employed in their monomeric and polymeric form as flame retardant additives and/or concentrates for normally flammable resinous materials, or can be copolymerized to yield flame or fire retardant polymeric compositions which are thermally stable which can be readily molded or formed into fire retardant articles such as films, sheets, fibers, laminates, reinforced plastics, etc.

Other modifications and variations of the present invention are possible in light of the above teachings. It is, therefore, to be understood that changes may be made in the particular embodiments of the invention described herein and further understood that such changes are within the full intended scope of the invention as defined by the appended claims.

We claim:

1. An improved bromination process comprising adding at a temperature at least below about +20° C, bromine to 3,3', 4,4'-tetrasubstituted diphenoquinone of the formula

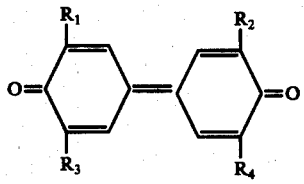

wherein independently each $R_1$, $R_2$, $R_3$ and $R_4$ substituent is selected from the group consisting of primary $C_{1-8}$ alkyl, primary $C_{1-8}$ alkoxy, phenyl and 4-bromophenyl in the presence of a liquid diluent, evolving hydrogen bromide gas at a temperature of at least about +15° C, heating the resulting reaction mixture at elevated temperatures to complete the bromination reaction, and recovering a 2,2',6,6'-tetrabromo-3,3',5,5'-tetrasubstituted-4,4'-biphenol, of the formula

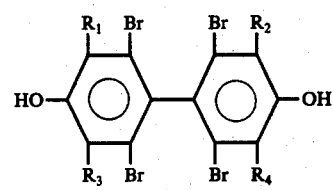

wherein $R_1$, $R_2$, $R_3$ and $R_4$ are as defined above, and further wherein the yield of the biphenol is at least about 70%.

2. The claim 1 process wherein the volume proportion of bromine to liquid diluent is at least within the range of from about 2.25:1 to about 1:2.25.

3. The claim 2 process wherein said diluent is a halogenated aliphatic hydrocarbon and the volume proportion of bromine to said diluent is within the range of from about 1.25:1 to about 1:1.25, wherein $R_1$, $R_2$, $R_3$ and $R_4$ are methyl substituents.

4. The claim 1 process comprising the steps:
  1. adding liquid bromine at a temperature below about 0° C. to said 3,3',5,5'-tetrasubstituted diphenoquinone, said bromine to diluent volume ratio being within the range of from about 2.25:1 to about 1:2.25, further wherein the bromine to diphenoquinone mole ratio is lower than about 6.5:1, thereby initiating and maintaining the evolution of gaseous hydrogen bromide at a substantially controlled rate at a temperature up to at least about +15° C.,
  2. subsequently contacting the resulting reaction mixture with additional bromine, heating the reaction mixture at elevated temperatures to complete the bromination reaction, and recovering said 2,2',6,6'-tetrabromo-3,3'5,5'-tetrasubstituted-4,4'-biphenol.

5. The claim 4 process, wherein step (1) the bromine to diphenoquinone mole ratio is lower than about 2.5:1, and $R_1$, $R_2$, $R_3$ and $R_4$ are methyl substituents.

6. The claim 1 process wherein the diluent is selected from carbon tetrachloride, chloroform, methylene chloride, tribromomethane, bromotrichloromethane, or trichloroethanol.

7. The claim 6 process wherein said diluent is carbon tetrachloride.

8. The claim 1 process further comprising steam distilling bromine from the reaction products.

9. The claim 1 process wherein said adding is carried out at a temperature below about 0° C.

* * * * *